United States Patent [19]

Ochsner et al.

[11] 4,006,108
[45] Feb. 1, 1977

[54] Z-ETHYL-3,6,6-TRIMETHYL-2-CYCLOHEX-ENE-1-CARBOXYLIC ACID ESTERS

[75] Inventors: Paul Albert Ochsner, Geneva; Hanspeter Schenk, Zumikon, both of Switzerland

[73] Assignee: Givaudan Corporation, Clifton, N.J.

[22] Filed: Apr. 14, 1975

[21] Appl. No.: 567,891

[30] Foreign Application Priority Data

Apr. 19, 1974 Switzerland .................. 5436/74
Feb. 13, 1975 Switzerland .................. 1772/75

[52] U.S. Cl. .................. 252/522; 260/343.2 R; 260/468 R
[51] Int. Cl.² .................. C11B 9/00
[58] Field of Search ......... 252/522; 260/468, 343.2

[56] References Cited
UNITED STATES PATENTS 3,890,370 6/1975 Buchi et al. .................. 252/522

Primary Examiner—Veronica O'Keefe
Attorney, Agent, or Firm—Thomas Cifelli, Jr.

[57] ABSTRACT

Novel odorants of the formula:

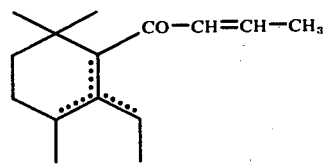

(I)

wherein one of three lines indicated by dots represents an additional bond.

The use of these compounds as odorants, process for the preparation of said compounds, and novel intermediates are also disclosed.

5 Claims, No Drawings

Z-ETHYL-3,6,6-TRIMETHYL-2-CYCLOHEXENE-1-CARBOXYLIC ACID ESTERS

FIELD OF THE INVENTION

This invention relates to novel odorants, intermediates therefor, and novel odorant compositions.

SUMMARY OF THE INVENTION

The novel odorants provided by the present invention have the formula I given in the Abstract of the Disclosure.

The novel compounds I may be prepared by processes disclosed hereinafter.

It will be appreciated that formula I hereinbefore embraces the following compounds Ia, Ib and Ic:

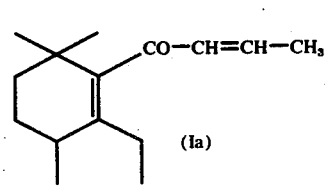
(Ia)

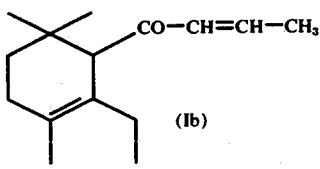
(Ib)

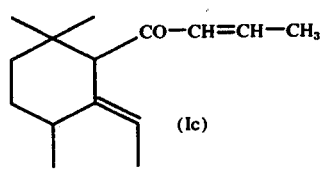
(Ic)

the cis-trans isomers, the configurational isomers and mixtures of such compounds.

According to the process provided by the present invention, the compounds of formula I hereinbefore are manufactured by a. oxidising an alcohol of the general formula

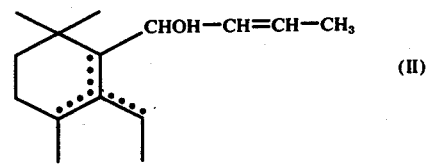
(II)

, wherein the lines indicated by dots have the significance given earlier, or b. isomerising the double bond in the 3,4-position of the side-chain of a compound of the general formula

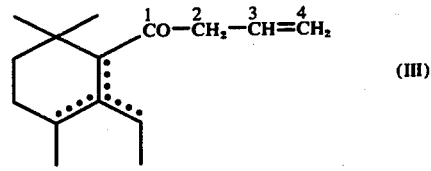
(III)

, wherein the lines indicated by dots have the significance given earlier, or c. acylating a metal-organic compound of the general formula Me—CH=CH—CH$_3$ (IVa)

or

Me—CH$_2$—CH=CH$_2$ (IVb)

, wherein Me represents a metallic function such as Li, Zn, Cd or Mg, with a substituted-cyclogeranoyl derivative of the general formula

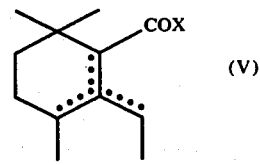
(V)

, wherein X represents a leaving atom or group (e.g. a halogen atom or an —O—alkyl, —O—aryl, —O—CO—aryl or —O—CO—alkyl group) and the lines indicated by dots have the significance given earlier, and isomerising the product obtained when a metal-organic compound of formula IVb is used, or d. treating the ketone of the formula (CH$_3$)$_2$C=CHCH$_2$CH(CH$_3$)—C(C$_2$H$_5$)=CHCOCH=CHCH$_3$ (VI)

with an acidic cyclisation agent, or e. partially hydrogenating a ketone of the general formula

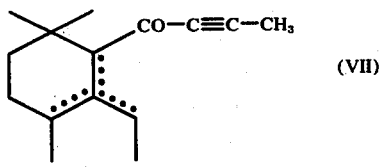
(VII)

, wherein the lines indicated by dots have the significance given earlier, at the triple bond.

The oxidation of an alcohol of formula II according to embodiment (a) of the process can be carried out according to methods known per se. Suitable oxidising agents are, for example, silver carbonate in the presence of diatomaceous earth and oxygen-containing derivatives such as oxides of transition metals (e.g. of chromium, manganese or nickel). An especially preferred oxidising agent is manganese dioxide/pyridine [J. R. Holum, J. Org. Chem. 26, 4814 (1961)]. In this method, the oxidation is preferably carried out at room temperature in an inert solvent (e.g. pentane or hexane). Moreover, chromium trioxide is also preferred.

When manganese dioxide is used as the oxidising agent, the geometric configuration of the starting material (cis- or trans alcohol of formula II or mixtures of same) is almost completely preserved. When chromium trioxide is used, preferably in the presence of an organic base such as pyridine, the ketone obtained has a trans-configuration irrespective of whether the alcohol starting material of formula II has a cis- or trans-configuration.

The isomerisation of the double bond in the 3,4-position of the side-chain of a compound of formula III according to embodiment (b) of the process can be carried out according to methods known per se with the aid of an acidic or basic isomerisation agent or by heating.

Suitable acidic isomerisation agents are, for example, strong mineral acids (e.g. sulphuric acid, phosphoric acid, perchloric acid, hydrogen chloride etc) and organic acids (e.g. p-toluenesulphonic acid, trifluoroacetic acid etc). The acidic isomerisation can be carried out in an organic solvent such as an aliphatic or aromatic hydrocarbon, which may be chlorinated, an ester or an ether. Benzene is expediently used.

Suitable basic isomerisation agents are inorganic bases such as alkali metal hydroxides (e.g. sodium hydroxide etc), alkaline earth metal hydroxides (e.g. calcuim hydroxide etc) and organic bases such as amines (e.g. dimethylaniline).

The acylation of a metal-organic compound of formula IVa or IVb with a cyclogeranoyl derivative of formula V according to embodiment (c) of the process can be carried out according to methods known per se. As the cyclogeranoyl derivative of formula V, there is preferably used a halide (e.g. a chloride, bromide or iodide) or a cyclogeraniate (e.g. a methyl, ethyl or alkali metal cyclogeraniate).

In embodiment (c) of the process, a metal-organic compound of formula IVa or IVb is expediently first added to an inert solvent (e.g. a hydrocarbon such as benzene or toluene) and the cyclogeranoyl derivative of formula V is then added, expediently at room temperature. In order to ensure complete reaction, the mixture is subsequently heated, for example to the reflux temperature of the mixture; see, for example, Buchi et al, Helv. Chim. Acta 54, 1767 (1971).

The product obtained from a metal-organic compound of formula IVb is expediently isomerised by alkaline treatment according to methods known per se; for example, by treatment with potassium carbonate/acetone, potassium tert.butylate/tert.butanol etc.

The acidic cyclisation of the ketone of formula VI according to embodiment (d) of the process can be carried out according to methods known per se.

As the acidic cyclisation agent there can be used a protonic acid such as a mineral acid (e.g. phosphoric acid or sulphuric acid), an organic acid (e.g. formic acid) or a Lewis acid (e.g. aluminium chloride, zinc chloride, boron trifluoride etherate, boron trifluoride, tin tetrachloride etc). [See, for example, Bedoukian, Perfumery and Flavouring Synthetics, Elsevier, New York (1967)]. The cyclisation is preferably carried out using tin tetrachloride in an inert solvent (e.g. benzene or toluene).

The partial hydrogenation of the triple bond of a ketone of formula VII according to embodiment (e) of the process can be carried out according to methods known per se. The partial hydrogenation can be carried out in the presence of the Lindlar catalyst [deactivated palladium-on-carbon: Helv. Chim. Acta 35, 446 (1952)]. The resulting compound of formula I has the cis-configuration in the side-chain.

If desired, the corresponding trans-isomers can be obtained by isomerising the cis-isomers using an acid in an inert solvent. The isomerisation can be carried out by means of a protonic acid, especially those acids which enolise ketones in a known manner such as p-toluenesulphonic acid, trifluoroacetic acid and hydrochloric acid. However, Lewis acids such as boron trifluoride or iodine can also be used. The isomerisation is expediently carried out in an inert solvent (e.g. an aromatic hydrocarbon such as benzene or toluene, an aliphatic or cycloaliphatic hydrocarbon such as heptane or cyclohexane or an ether such as monoglyme, diglyme or dioxane). The temperature at which the isomerisation is carried out is not critical. The isomerisation can be carried out, for example, by mixing the substance to be isomerised with the solvent and a catalytic amount of the acidic isomerisation agent and the mixture left to stand at room temperature for several hours (e.g. 12 hours).

The compounds of formula I or their isomeric mixtures possess particular odorant properties. Thus, for example, the odour of a mixture of the compounds of formula Ia, Ib and Ic is typically agrestic (rustic), with the odour notes being characterised as: towards tobacco and eucalyptus seeds, smoky (isoeugenol), fruity.

These odour notes are surprisingly completely different from those of the closely structurally related 2,3,6,6-tetramethyl-1-crotonyl-cyclohexene-(1 and 2), which is known from DOS 2,022,216. That isomeric mixture provides, in particular, a woody note, somewhat reminiscent of quinoline and nuts, weakly spice-like.

Because of their interesting olfactory properties, the compounds of formula I or their isomeric mixture can be used as odorants; for example, in perfumery for the manufacture of odorant compositions such as perfumes or for perfuming products of a variety of types such as, for example, soaps, washing agents, solid and liquid detergents, aerosols or other cosmetic products such as ointments, face milk, make-up, lipsticks, bath salts, bath oils etc.

Because of its very natural notes, the isomeric mixture of compounds of formula I is especially suitable for modifying known compositions; for example, those of the chypre type. It is very well suited to combine with wood notes such as those obtainable, for example, when using p-tert.butylcyclohexyl acetate, sandalwood oil, patchouli oil, cedryl acetate, methyl ionone etc.

Depending on the intended use, the concentration of the mixture of compounds of formula I can vary within wide limits; for example, between about 1 wt.% (detergents) and about 15 wt.% (alcoholic solutions). In perfume bases or concentrates, the concentrations can, of course, also be higher.

It will accordingly be appreciated that the present invention includes within its scope:

a. an odorant composition which contains as an essential odour-imparting ingredient a compound of formula I hereinbefore, and b. a method of imparting an odour to materials by applying thereto or incorporating therein an odour-imparting amount of a compound of formula I hereinbefore.

In a further aspect of the present invention, it has been found that those cyclogeranoyl derivatives of formula V required as starting materials for embodiment C) of the foregoing process, in which X represents —O—($C_{1-4}$ alkyl) or —O—aryl likewise possess valuable odorant properties and can be used as odorants on account of their interesting olfactory properties.

The cyclogeranoyl derivatives referred to in the preceding paragraph are novel and also form part of this invention. They can be generically formulated thus:

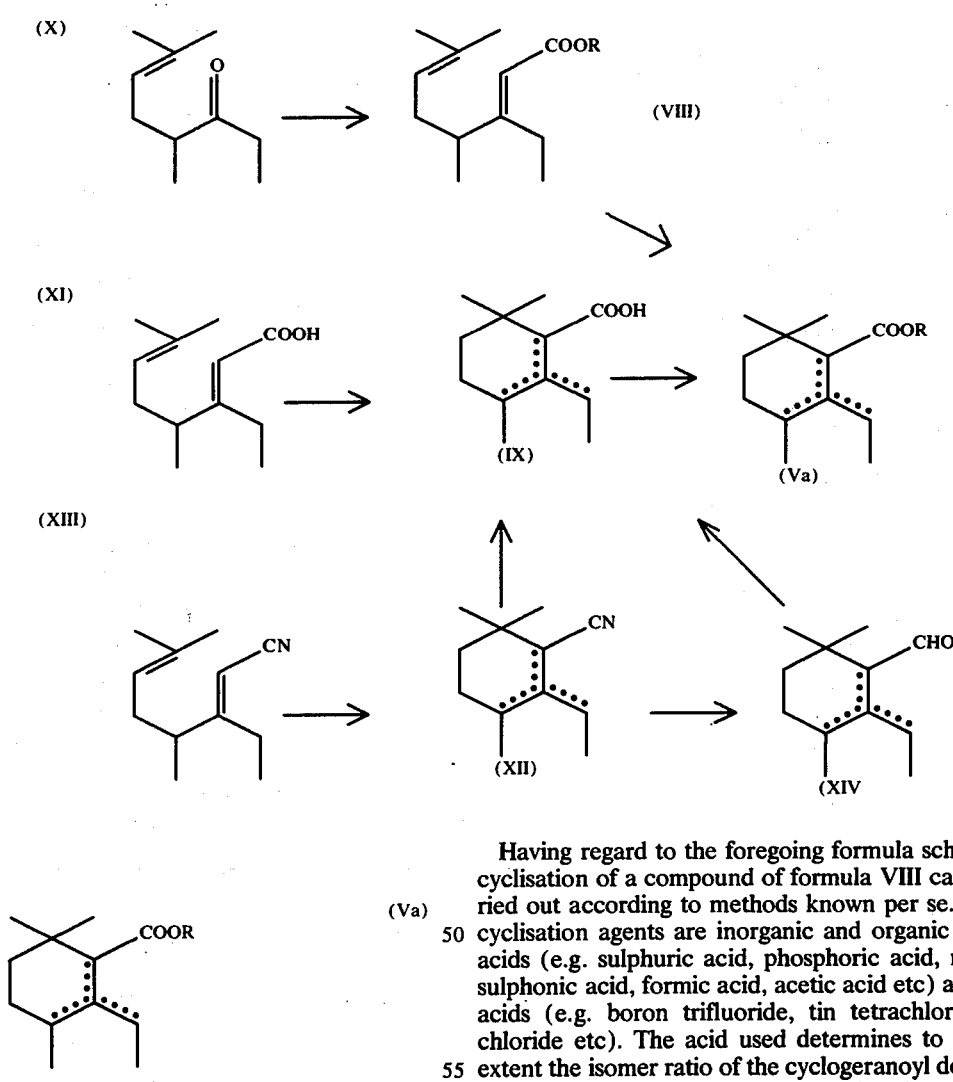

wherein R represents a $C_{1-4}$ alkyl or aryl, especially phenyl, group and the lines indicated by dots have the significance given earlier.

The odorant properties of the cyclogeranoyl derivatives of formula V$a$ resemble those of the compounds of formula I. In the case of these cyclogeranoyl derivatives, e.g. in case of compound (V$a$), where R = ethyl, the slightly fruity and tobacco-like notes and, in particular, the note reminiscent of eucalyptus seeds are noteworthy.

The cyclogeranoyl derivatives of formula V$a$ hereinbefore can be used for the same purposes as the compounds of formula I. It will thus be appreciated that the invention includes within its scope:

a. an odorant composition which contains as an essential odour-imparting ingredient a cyclogeranoyl derivative of formula V$a$ hereinbefore, and b. a method of imparting an odour to materials by applying thereto or incorporating therein an odour-imparting amount of a cyclogeranoyl derivative of formula V$a$.

The cyclogeranoyl derivatives of formula V$a$ can be prepared according to methods known per se. The preparation is illustrated in the following formula scheme in which R and the lines indicated by dots have the significance given earlier;

Having regard to the foregoing formula scheme, the cyclisation of a compound of formula VIII can be carried out according to methods known per se. Suitable cyclisation agents are inorganic and organic protonic acids (e.g. sulphuric acid, phosphoric acid, methanesulphonic acid, formic acid, acetic acid etc) and Lewis acids (e.g. boron trifluoride, tin tetrachloride, zinc chloride etc). The acid used determines to a certain extent the isomer ratio of the cyclogeranoyl derivatives of formula V$a$. Thus, for example, formic acid with a 10% content of concentrated sulphuric acid gives primarily the α-isomer and phosphoric acid gives a mixture in which the α- and γ-isomers predominate.

The cyclisation can be carried out in the presence or absense of a solvent. Suitable solvents are inert solvents such as hexane, benzene, nitromethane etc. The temperature is not critical. The cyclisation can be carried out at room temperature or at a temperature above or below room temperature.

The compounds of formula VIII are conveniently prepared from 4,7-dimethyl-6-octen-3-one of formula X. For example, this ketone can be reacted with an appropriate carbalkoxy-methylenediethylphosphonate under the conditions of a Horner-Wittig reaction [Wadsworth/Emmons modification, J. Amer. Chem. Soc. 83, 1733 (1961)] in the presence of an alkali hydride or alkali alcoholate as the base.

The reaction is expediently carried out in an aprotic solvent such as benzene, toluene, dimethoxyethane etc. The temperature at which the reaction is carried out is not critical. It is preferred to carry out the reaction at a temperature of ca 40°–60° C, but it can also be carried out a lower or higher temperature.

It is also possible to react 4,7-dimethyl-6-octen-3-one with bromoacetic ester/zinc under the conditions of a Reformatzky reaction and to cleave water from the primarily formed hydroxy ester. This reaction is conveniently carried out in an inert solvent such as diethyl ether, benzene, toluene etc. The water cleavage from the initially obtained hydroxy ester is preferably carried out using phosphorus tribromide in pyridine [Shriner, Organic Reactions, 1, 1 (1947)].

The esterification of an acid of formula IX is conveniently carried out by treatment of a salt thereof (e.g. an alkali salt) with an appropriate alkyl halide (e.g. ethyl iodide) in alcohol [see, for example, Houben-Weyl, Methoden der organischen Chemie VIII, 541 (1952)]. The temperature at which this treatment is carried out is not critical, but it is expedient to carry out the reaction at room temperature.

An acid of formula IX is obtained from the acid of formula XI or from a nitrile of formula XIII, if necessary via an aldehyde of formula XIV. The cyclisation of the acid of formula XI can be carried out under the conditions mentioned earlier for the cyclisation of a compound of formula VIII. The cyclisation of a nitrile of formula XIII can also be carried out in a similar manner. A cyclic nitrile of formula XII can be saponified to an acid of formula IX according to known methods (e.g. using an alkali). A cyclic nitrile of formula XII can also be converted into an aldehyde of formula XIV, for example by reduction using diisobutyl aluminium hydride [Miller et al, J. Org. Chem. 24, 627 (1959)]. The reduction is conveniently carried out in an inert solvent such as hexane or toluene and preferably at room temperature. The aldehyde obtained is then oxidised to an acid of formula IX, conveniently using silver nitrate/alkali [see, for example, Walborsky et al., J. Amer. Chem. Soc. 73, 2593 (1951)]. This oxidation is conveniently carried out in an alcohol/water mixture and at room temperature.

The $C_{1-4}$ alkyl esters of formula VIII, the acids of formula IX, the cyclic nitriles of formula XII and the aldehydes of formula XIV are novel and it will be appreciated that they also form part of this invention.

The following Examples illustrate the present invention:

EXAMPLE 1

2.7 kg of dry hexane, 1 kg of manganese dioxide [J. Chem. Soc. (1952), 1104] and 100 g of 2-ethyl-3,6,6-trimethyl-1-(1-hydroxy-2-butenyl)-2-cyclohexene (containing ca 85% α-isomer) are added to a round-bottomed flask which is provided with a stirrer and thermometer. The mixture is tirred for 48 hours at 20° C. The mixture is subsequently filtered over diatomaceous earth and rinsed with ether. The solvent of the filtrate is removed by distillation and there are thus obtained 95 g of crude material. By distillation, there are obtained 58.8 g (= 58,9% yield) of olfactorily pure material in form of an isomeric mixture containing 85% of 2-ethyl-3,6,6-trimethyl-1-crotonoyl-2-cyclohexene (so-called α-isomer) of boiling point 63°–66° C/0.07-1 mm Hg, $n_D^{20}$ = 1.4945-1.4959.

The 2-ethyl-3,6,6-trimethyl-1-(1-hydroxy-2-butenyl)-2-cyclohexene used as the starting material can be prepared as follows:

162 g (0.9 mol) of 3-ethyl-4,7-dimethyl-octa-2,6-dienal and 220 ml of diethyl ether are added to a round-bottomed flask which is equipped with a thermometer and stirrer. 102 g (1.1 mol) of freshly distilled aniline are added dropwise with stirring and the mixture is then stirred for a further 1.5 hours. The water formed is decanted off and the ethereal solution of the Schiff's base formed is dried over sodium sulphate.

880 g of concentrated sulphuric acid are cooled to −20° C in a round-bottomed flask under a nitrogen atmosphere. The ethereal solution of the Schiff's base is now added within 1 hour at this temperature. The mixture is stirred for a further 30 minutes at −20° C and poured on to 1.5 kg of crushed ice. The mixture is extracted with ether, washed three times with water, then with a 10% sodium carbonate solution and finally once again with water. After evaporation of the ether, there remain 128 g of crude 2-ethyl-3,6,6-trimethyl-1-formyl-2-cyclohexene which, after fractional distillation, produces 62.2 g (38.4%) of the pure material (containing 85% α-isomer); boiling point 83°–88° C; $n_D^{20}$ = 1.4773.

25.2 g (1.05 g-atoms) of magnesium shavings in 80 ml of dry tetrahydrofuran are added to a round-bottomed flask which is provided with a stirrer, condenser, thermometer and dropping funnel. 133.1 g (1.1 g-atoms) of 1-propene bromide in 150 ml of dry tetrahydrofuran are now slowly added with stirring. The mixture is brought to reflux temperature for 30 minutes and then left to cool (12 hours). A solution of 180.3 g (1 mol) of the aldehyde obtained according to the preceding paragraph in 250 ml of dry tetrahydrofuran is now added at 10° C. The mixture is held at 40° for 6 hours, again left to cool, moist ether is added and the mixture decomposed by means of a saturated ammonium chloride solution. The organic layer is washed with water, with tartaric acid and then again with water. After evaporation of the solvent, there are obtained 239 g of crude 2-ethyl-3,6,6-trimethyl-1-(1-hydroxy-2-butenyl)-2-cyclohexene (containing ca 85% α-isomer), distillation of which produces 117 g (53%) of pure product of boiling point 88°–95° C/0.2 mm Hg; $n_D^{20}$ = 1.4923-1.4942.

EXAMPLE 2

50 g (0.224 mol) of c,t-3-ethyl-4,7-dimethyl-2,6-octadienoic acid ethyl ester are cautiously added to a solution, cooled to 5°–10° C, of 450 ml of concentrated formic acid and 50 ml of concentrated sulphuric acid. After completion of the addition, the mixture is left to come to room temperature. It is then stirred at room temperature for 1 hour. The mixture is poured on to ice and extracted three times with hexane. The combined hexane extracts are washed once with water, twice with sodium bicarbonate solution and three times with water, dried over sodium sulphate and evaporated. The crude product (49.1 g) is fractionally distilled. There are obtained 37 g (72%) of pure 2-ethyl-3,6,6-trimethyl-2-cyclohexene-1-carboxylic acid ethyl ester of boiling point 63°–64° C/0.05 mm Hg; $n_D^{20}$ = 1.4645.

The c,t-3-ethyl-4,7-dimethyl-2,6-octadienoic acid ethyl ester used as the starting material can be obtained as follows:

A solution of 13.6 g (0.59 g-atoms) of sodium in 335 ml of ethanol is placed in a 4-necked flask which is provided with a mechanical stirrer, dropping funnel and thermometer. A solution of 77 g (0.5 mol) of 4,7-dimethyl-6-octen-3-one and 145.6 g (0.65 mol) of carbethoxymethylenediethylphosphonate in 300 ml of toluene is added dropwise to the flask at 0°–10° C within 1.5 hours. The mixture is then warmed to 40°–45° C for 15 hours and to 60° C for 5 hours. The mixture is then poured on to ice-water and extracted three times with hexane. The combined hexane extracts are washed three times with water, dried over sodium sulphate and evaporated. The crude product is fractionally distilled. At 67°–69° C/0.05 mm Hg there are obtained 76.2 g (67%) of pure c,t-3-ethyl-4,7-dimethyl-2,6-octadienoic acid ethyl ester; $n_D^{20}$ = 1.4667.

EXAMPLE 3

A mixture of 81 ml of concentrated formic acid and 9 ml of concentrated sulphuric acid is cooled to 5°–10° C and there are cautiously added at this temperature 10 g (39.7 mmol) of 3-ethyl-4,7-dimethyl-2,6-octadienoic acid n-butyl ester. The mixture is left to come to room temperature and then stirred at room temperature for ca 1 hour. The mixture is then poured on to ice extracted three times with hexane. The combined hexane solutions are washed once with water, twice with sodium bicarbonate solution and three times with water, dried over sodium sulphate and concentrated. The crude product (9.1 g) is fractionally distilled. There are obtained 6.9 g (69%) of pure 2-ethyl-3,6,6-trimethyl-2-cyclohexene-1-carboxylic acid n-butyl ester of boiling point 73°–74° C/0.03 mm Hg; $n_D^{20}$ = 1.4663. The ester has a powerful balsamic and spicy odor with a slight buttery undertone.

The 3-ethyl-4,7-dimethyl-2,6-octadienoic acid n-butyl ester used as the starting material can be obtained by trans-esterifying the corresponding ethyl ester as follows:

A solution of 100 mg of sodium in 85 ml of n-butanol is placed in a flask filled with nitrogen and cooled to ca 5° C. At this temperature, 20 g (0.09 mol) of 3-ethyl-4,7-dimethyl-2,6-octadienoic acid ethyl ester are added. The mixture is then warmed to 60° C for 5 hours and to 100° C for 3 hours. For the working-up, the mixture is acidified with a few drops of glacial acetic acid and then the major part of the n-butanol is distilled off on a rotary evaporator. The residue is taken up in n-hexane, washed twice with sodium bicarbonate solution and three times with water, dried over sodium sulphate and evaporated. The crude product (19.3 g) is fractionally distilled. There are obtained 16.4 g (73%) of pure 3-ethyl-4,7-dimethyl-2,6-octadienoic acid n-butyl ester of boiling point 90°–92° C/0.04 mm Hg; $n_D^{20}$ = 1.4677.

EXAMPLE 4

A few crystals of diphenyl are added to a suspension, cooled to 5°–10° C and held under a nitrogen atmosphere, of 2.4 g (0.35 g-atoms) of finely cut lithium wire in 40 ml of absolute tetrahydrofuran. 2 ml of a solution of 9.4 g (70 mmol) of allyl phenyl ether in 10 ml of absolute ether are then added. After a greenish coloration sets in, the rest of the solution is added dropwise at −15° C. After completion of the addition, the mixture is stirred for 30 minutes at 0° C. The resulting allyl lithium solution is decanted off from excess lithium and transferred to a dropping funnel. This solution is added dropwise to a solution, cooled to −60° C and maintained under nitrogen, of 4.48 g (20 mmol) of 2-ethyl-3,6,6-trimethyl-2-cyclohexene-1-carboxylic acid ethyl ester in 40 ml of absolute ether. After completion of the addition, the mixture is left to warm to room temperature, poured on to ice-water and extracted with three portions of hexane. The combined hexane extracts are washed neutral with three portions of water, dried over sodium sulphate and evaporated. By fractional distillation of the residue there are obtained 3.75 g (85%) of 2-ethyl-3,6,6-trimethyl-1-[but-3-enoyl]-2-cyclohexene; boiling point 57°–58° C/0.04 mm Hg; $n_D^{20}$ = 1.4865.

A suspension of 3.5 g (15.9 mmol) of 2-ethyl-3,6,6-trimethyl-1-[but-3-enoyl]-2-cyclohexene and 2.0 g of potassium carbonate in 40 ml of acetone is stirred at room temperature under nitrogen for 24 hours. The salt is removed by filtration and the filtrate concentrated. After fractional distillation, the residue yields 3.2 g (91.5%) of 2-ethyl-3,6,6-trimethyl-1-crotonoyl-2-cyclohexene; boiling point 59°–60° C/0.04 mm Hg; $n_D^{20}$ = 1.4952.

Example 5

| Odorant composition (chypre) | Parts by weight |
|---|---|
| Compounds I (distilled isomeric mixture, Ex. 1) | 100 |
| Styrallyl acetate | 20 |
| Methylnonylacetaldehyde (10% in diethyl phthalate) | 20 |
| Vetiveryl acetate | 50 |
| Rhodinol | 50 |
| Patchouli oil | 50 |
| Tree Moss Absolue (50% in diethyl phthalate) | 50 |
| p-tert.Butyl-α-methylhydrocinnamaldehyde | 100 |
| Hydroxycitronellal | 100 |
| Methylionone | 100 |
| Musk ambrette | 100 |
| Coumarin | 100 |
| Bergamotte oil Reggio | 100 |
| | 1000 |

The odorant note of the composition is woody, somewhat reminiscent of dried herbs, faintly towards withered blossoms. The composition is suitable, for example, for the perfuming of shaving waters.

EXAMPLE 6

| Flowery Composition | Parts by weight |
|---|---|
| 2-Ethyl-3,6,6-trimethyl-2-cyclohexen-1-carboxylic acid ethyl ester | 100 |
| Laurine | 760 |
| Linalool | 70 |
| N-Hexyl Salicylate | 30 |
| Cyclamen Aldehyde | 20 |
| Galbanum Oil conc. | 20 |
| | 1000 |

By addition of 2-ethyl-3,6,6-trimethyl-2-cyclohexene-1-carboxylic acid ethyl ester, the composition is more vivacious and more diffusive.

What is claimed is:

1. A cyclogeranoyl compound of the general formula

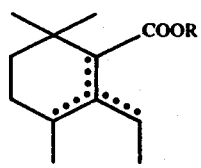

(Va)

wherein R represents a $C_{1-4}$ alkyl or phenyl group and one of the three lines indicated by dots represents an additional bond.

2. 2-Ethyl-3,6,6-trimethyl-2-cyclohexene-1-carboxylic acid ethyl ester.

3. 2-Ethyl-3,6,6-trimethyl-2-cyclohexene-1-carboxylic acid n-butyl ester.

4. An odorant composition comprising as one of its olfactory ingredients an olfactorily-effective amount of a cyclogeranoyl compound of formula V$a$ given in claim 1.

5. Compounds in accordance with claim 1 wherein R is phenyl.

* * * * *